(12) United States Patent
Yoneto et al.

(10) Patent No.: US 8,609,134 B2
(45) Date of Patent: *Dec. 17, 2013

(54) METHODS OF TRANSDERMALLY ADMINISTERING AN INDOLE SEROTONIN RECEPTOR AGONIST AND TRANSDERMAL COMPOSITIONS FOR USE IN THE SAME

(75) Inventors: Kunio Yoneto, San Jose, CA (US); Katsuyuki Inoo, Kagawa (JP)

(73) Assignee: Teikoku Pharma USA, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/877,848

(22) Filed: Sep. 8, 2010

(65) Prior Publication Data

US 2011/0002967 A1 Jan. 6, 2011

Related U.S. Application Data

(63) Continuation of application No. 11/561,235, filed on Nov. 17, 2006, now Pat. No. 7,816,394.

(60) Provisional application No. 60/752,767, filed on Dec. 20, 2005, provisional application No. 60/790,451, filed on Apr. 6, 2006.

(51) Int. Cl.
*A61K 9/70* (2006.01)
*A61F 13/00* (2006.01)

(52) U.S. Cl.
USPC .......................................... 424/449; 514/415

(58) Field of Classification Search
USPC .......................................... 424/449; 514/415
See application file for complete search history.

(56) References Cited

U.S. PATENT DOCUMENTS

| 5,807,571 | A | 9/1998 | List |
| 6,579,898 | B2 | 6/2003 | Humphrey |
| 6,814,976 | B1 | 11/2004 | Hille et al. |
| 6,955,819 | B2 | 10/2005 | Zhang et al. |
| 2003/0013753 | A1 | 1/2003 | Aung-Din |
| 2004/0096491 | A1 | 5/2004 | Tateishi et al. |
| 2004/0258740 | A1 | 12/2004 | Thompson |
| 2005/0042271 | A1 | 2/2005 | Xiong et al. |
| 2005/0260255 | A1 | 11/2005 | Terahara et al. |

FOREIGN PATENT DOCUMENTS

| CA | 2160776 | 11/1994 |
| CN | 1499962 A | 5/2004 |
| EP | 1541177 | 6/2005 |
| JP | 08319234 | 12/1996 |
| JP | 2004292379 | 10/2004 |
| WO | 02069942 | 9/2002 |

OTHER PUBLICATIONS

Osborne (Pharmaceutical Technology Nov. 1997).*
Pringhseim et al., "Triptans: Are they all the same?" Migraine Headache (2002), p. 140-146.
Walling "Comparing Oral Triptans" Treatment of Acute Migraine (2002).
Pini et al. Journal of Headache Pain (2001) S103-106.
Femenia-Font, et al., "Effect of chemical enhancers on the in vitro percutaneous absorption of sumatriptan succinate" European Journal of Pharmaceutics and Biopharmaceutics 61 (2005) 50-55.
Femenia-Font et al., "Iontophoretic Transdermal Delivery of Sumatriptan: Effect of Current Density and Ionic Strength" Journal of Pharmaceutical Sciences, vol. 94, No. 10 (2005) pp. 2183-2186.

* cited by examiner

*Primary Examiner* — Sreeni Padmanabhan
*Assistant Examiner* — Irina Neagu
(74) *Attorney, Agent, or Firm* — Rudy J. Ng; Bret E. Field; Bozicevic Field & Francis, LLP

(57) ABSTRACT

Methods of transdermally delivering a therapeutic amount of an indole serotonin receptor agonist to an individual in need thereof, e.g., to provide a therapeutic level of an indole serotonin receptor agonist to an individual in need thereof, are provided. Also provided are transdermal formulations of indole serotonin receptor agonists that find use in practicing the subject methods.

22 Claims, 3 Drawing Sheets

METHODS OF TRANSDERMALLY ADMINISTERING AN INDOLE SEROTONIN RECEPTOR AGONIST AND TRANSDERMAL COMPOSITIONS FOR USE IN THE SAME

CROSS-REFERENCE TO RELATED APPLICATIONS

Pursuant to 35 U.S.C. §119 (e), this application filed on 8 Sep. 2010, is a Continuation of application Ser. No. 11/561,235, filed on 17 Nov. 2006, now U.S. Pat. No. 7,816,394, which claims priority to the filing dates of: U.S. Provisional Patent Application Ser. No. 60/752,767 filed Dec. 20, 2005 and U.S. Provisional Patent Application Ser. No. 60/790,451 filed on Apr. 6, 2006; the disclosures of which are herein incorporated by reference.

INTRODUCTION

Triptan-type drugs, which are modified forms of serotonin (5-hydroxytryptamine; 5-HT), have been developed for the treatment of migraine headaches. Triptan-type drugs are serotoninergic agents that exhibit receptor-selective properties. Although the principal mechanism of action of triptan-type drugs is still under research, it is understood that they relieve the various symptoms of a migraine headache by inhibiting the over activity of trigeminal nerve terminals through serotonin 5-HT1B, 5-HT1D, 5-HT1F receptors that exist in blood vessels in the brain and trigeminal nerves; and by inhibiting inflammation around blood vessels, hyperlucency and vasodilation.

Various formulations, such as injection formulations, oral formulations (e.g., tablets), and nasal formulations (e.g., nasal drops), have been developed for administration of triptan-type drugs. Nevertheless, there is continued interest in development of new delivery systems for triptan type drugs.

SUMMARY

Methods of transdermally delivering a therapeutic amount of an indole serotonin receptor agonist to an individual in need thereof, e.g., to provide a therapeutic level of an indole serotonin receptor agonist to an individual in need thereof, are provided. Also provided are transdermal formulations of indole serotonin receptor agonists that find use in practicing the subject methods.

DEFINITIONS

Figure 1:
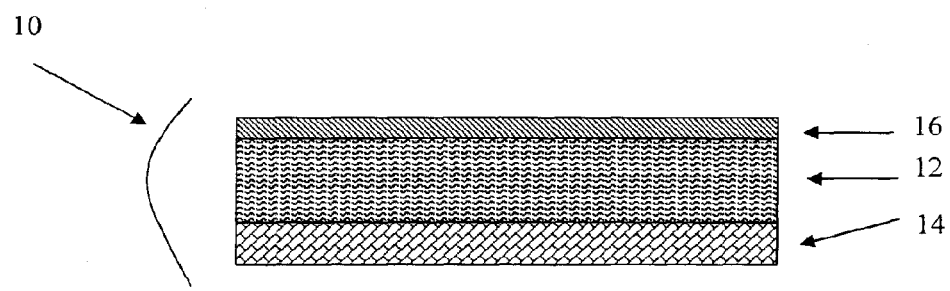
FIG. 1 provides a cross-sectional view of a transdermal patch preparation according to the invention.

As used herein, the term "headache" includes migraine headache, cluster headaches, rebound headaches, and status migrainosus. "Migraine headache" refers to a subset of headaches characterized by unusually severe, unilateral, throbbing, headache pain, usually persisting for 4 hours to 72 hours, and often including one or more of the following symptoms: nausea, vomiting, sensitivity to light or sound. "Relapse headache" variously and interchangeably termed a "rebound," "relapse," "recurrent," "follow on," or "secondary" headache refers to headaches experienced by migraine patients after having experienced initial relief. A relapse headache may occur from 1 hour to 24 hours following initial relief from a migraine headache. Status migrainosus refers to a condition in which a patient, often with a previous history of migraine, suffers a continuous migraine. In status migrainosus, the pain is typical, unilateral and throbbing, and the patient is often disabled.

As used herein, the term "indole serotonin receptor agonist" is used interchangeably with "triptan-type drug" and refers to an agent that has affinity for one or more of a 5-HT1B receptor, a 5-HT1D receptor, and a 5-HT1F receptor; and effects vasoconstriction of cerebral blood vessels and/or inhibition of pro-inflammatory neuropeptide release. An indole serotonin receptor agonist comprises a indole-3-alkylamine structure, as described in more detail below.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

DETAILED DESCRIPTION

Methods of transdermally delivering a therapeutic amount of an indole serotonin receptor agonist to an individual in need thereof, e.g., to provide a therapeutic level of an indole serotonin receptor agonist to an individual in need thereof, are provided. Also provided are transdermal formulations of indole serotonin receptor agonists that find use in practicing the subject methods.

In further describing the invention, embodiments of the methods will be reviewed first in greater detail, followed by a discussion of aspects of various transdermal formulations that may find use in practicing embodiments of the methods.

Methods

The present invention provides methods of delivering a therapeutic amount of an indole serotonin receptor agonist to an individual in need thereof. Aspects of the methods include contacting a topical surface of an individual with a suitable formulation of the indole serotonin receptor agonist, where the formulation may be viewed as a transdermal formulation. The topical surface is generally a skin surface, such that embodiments of the invention include contacting a skin surface of an individual with a transdermal formulation of the indole receptor serotonin agonist in a manner sufficient to deliver a therapeutic amount of the agonist to the individual.

The transdermal formulation employed in embodiments of the methods may vary. Transdermal formulations of interest include, but are not limited to: patch formulations, such as adhesive polymer formulations (which may also be referred to as tapes and plasters); gels; creams; foams; lotions; sprays; ointments; etc.

In practicing the invention, the transdermal formulation is applied to any convenient skin surface. Skin surfaces of interest include, but are not limited to: arms, leg, torso, head, neck, etc. The surface area that is covered by the transdermal formulation following application is generally sufficient to provide for the desired amount of agent administration, and in certain embodiments ranges from about 1 cm$^2$ to about 200 cm$^2$. In certain embodiments, the transdermal formulation is applied to a keratinized skin site of the host proximal to target nerves associated with the headache pain. The skin site at which the formulation is applied is, in certain embodiments, sufficiently proximal to the target nerves, e.g. the skin site overlies the region innervated by the target nerves, so that upon contact of the composition with the skin surface, the active agent can readily reach the target nerves and exert its anti-conduction activity. Of interest as skin sites of transdermal application in certain embodiments are the supraorbital and occipital regions, where in embodiments the transdermal formulation is applied to a forehead skin of the subject.

A subject delivery method will, in certain embodiments, provide a therapeutic level of an indole serotonin receptor agonist, e.g., a level of an indole serotonin receptor agonist that is sufficient to inhibit, prevent, or reduce headache pain. In some embodiments, a transdermal formulation, when applied to a skin surface of an individual, will provide a therapeutic level of an indole serotonin receptor agonist over an extended period of time, e.g. over a period of time of from about 1 hour to about 1 week. In certain embodiments, a transdermal formulation, when applied to a skin surface of an individual, will provide a therapeutic level of an indole serotonin receptor agonist over an extended period of time, where the therapeutic level of the indole serotonin receptor agonist remains relatively constant in the individual over the extended period of time. A "relatively constant" level is a level that varies by no more than about 30%, e.g., less than about 25%, less than about 20%, or less than about 15%, over a given period of time. By extended period of time is meant a time about 0.5 days or longer, such as about 2 days or longer, e.g., a time ranging from about 0.5 days to about 2 weeks, such as from about 1 day to about 1 week. By "therapeutic level" is meant a level in plasma or other internal bodily tissue or fluid (e.g., cranial fluid, cerebrospinal fluid) that provides for reduction, inhibition, or prevention of headache pain.

In practicing the subject methods, a transdermal formulation may be applied a single time or a plurality of times over a given time period, e.g., the course of the disease condition being treated, where the dosing schedule when a plurality of patches are administered over a given time period may be daily, weekly, biweekly, monthly, etc.

In some embodiments, a subject delivery method treats a headache, e.g., the method is suitable for abortive therapy of a headache. In other embodiments, a subject delivery method prevents the occurrence of a headache. In some embodiments, a subject delivery method reduces or eliminates one or more symptoms of a migraine headache.

Individuals who are suitable for treatment with a subject delivery method include individuals suffering from migraine headache; and individuals who are prone to suffering from migraine headaches, e.g., individuals with a history of migraine headache. Individuals who are suitable for treatment with a subject delivery method also include individuals suffering from a rebound headache. Individuals who are suitable for treatment with a subject delivery method also include individuals suffering from status migrainosus. Individuals may be diagnosed as being in need of the subject methods using any convenient protocol, and are generally known to be in need of the subject methods prior to practicing the subject methods.

Generally, subjects suitable for treatment with a subject method are "mammals" or "mammalian." In certain embodiments, the individual will be a human. The term "individual" is used interchangeably herein with "patient."

Transdermal Delivery System

Aspects of the invention further include transdermal patch formulations, where the patch formulations of certain embodiments include an adhesive layer and a backing layer. The adhesive layer includes, in certain embodiments, an adhesive polymer base composition and an indole serotonin receptor agonist. In certain embodiments, the transdermal formulation further includes a hydrophobic oil.

FIG. 1 provides a representation of a subject transdermal delivery system. As can be seen in FIG. 1, this representative transdermal delivery system 10 contains a adhesive base 12 present on a support 14.

In these embodiments, the adhesive layer includes an indole serotonin receptor agonist in an amount that, when the transdermal delivery system is placed on the skin of an individual, provides for a level of the indole serotonin receptor agonist that is effective to treat a disorder in the individual. The adhesive layer may include an indole serotonin receptor agonist in an amount of from about 0.5 weight % to about 50 weight %, e.g., from about 0.5 weight % to about 5 weight %, from about 5 weight % to about 10 weight %, from about 10 weight % to about 20 weight %, from about 20 weight % to about 30 weight %, from about 30 weight % to about 40 weight %, or from about 40 weight % to about 50 weight %. In some embodiments, an indole serotonin receptor agonist is present in the adhesive layer in an amount of from about 1 weight % to about 30 weight %, from about 1 weight % to about 20 weight %, from about 1 weight % to about 10 weight %, from about 5 weight % to about 20 weight %, from about 5 weight % to about 30 weight %, from about 5 weight % to about 40 weight %, or from about 5 weight % to about 50 weight %.

Indole Serotonin Receptor Agonists

Suitable indole serotonin receptor agonists are of Formula I:

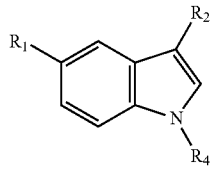

Formula I wherein $R_1$ is

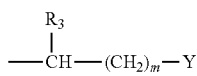

wherein Y is

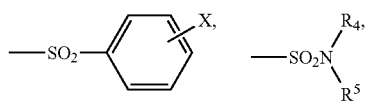

or a 5- or 6-membered cycloalkyl, wherein in some embodiments 1, 2, or 3 $CH_2$ groups are replaced by O, S, or NH, which cycloalkyl will in some embodiments by substituted with an oxo group;
X is H, C1-3-alkyl, C1-3-alkoxy, halogen, CF3, NO2 or NH2;
$R_3$ is H or C1-3-alkyl;
$R_4$ is H, C1-6-alkyl or C3-6-alkenyl;
$R_5$ is H, C1-3-alkyl, C3-6-alkenyl, aryl, aryl (C1-4alkylene or C5-7-cycloalkyl;
wherein $R_2$ is

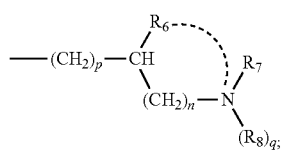

$R_6$ is H or $(CH_2)_r$;
$R_7$ and $R_8$ are the same or different, and are each independently H, or C1-3-alkyl;
$R_9$ is H, C1-6-alkyl, or C3-6-alkenyl;
m, n, and r may be the same or different and are each independently an integer from 0 to 3, e.g., are each independently 0, 1, 2, or 3;
p is an integer that is 0 or 1; and
q is an integer that is 0 or 1;

with the proviso that when $R_6$ is (CH2)r) and r is not zero, this group can be bound to the nitrogen atom of the radical $NR_7(R_8)_q$ by a single bond, in which case q is zero. In some embodiments, the indole serotonin receptor agonist is a physiologically acceptable salt of a compound of Formula I, or a solvate of a compound of Formula I, or a pro-drug of a compound of Formula I. In some embodiments, e.g., the agonist is a succinate salt of a compound of Formula I.

In some embodiments, the indole serotonin receptor agonist is a compound of Formula I, where $R_1$ is $CH_3HNSO_2CH_2$; $R_2$ is $—CH_2CH_2N(CH_3)_2$; and $R_4$ is H. This compound is referred to as Sumatriptan.

In some embodiments, the indole serotonin receptor agonist is a compound of Formula I, where $R_1$ is

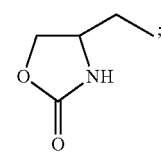

$R_2$ is $—CH_2CH_2N(CH_3)_2$; and $R_4$ is H. This compound is referred to as Zolmitriptan.

In some embodiments, the indole serotonin receptor agonist is a compound of Formula I, where $R_1$ is

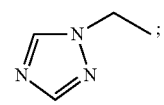

$R_2$ is $—CH_2CH_2N(CH_3)_2$; and $R_4$ is H. This compound is referred to as Rizatriptan.

In some embodiments, the indole serotonin receptor agonist is a compound of Formula I, where $R_1$ is $CH_3HNSO_2CH_2$, $R_2$ is

and $R_4$ is H. This compound is referred to as Naratriptan.

In some embodiments, the indole serotonin receptor agonist is a compound of Formula I, where $R_1$ is

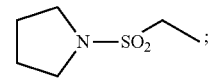

$R_2$ is $—CH_2CH_2N(CH_3)_2$; and $R_4$ is H. This compound is referred to as Almotriptan. In some embodiments, the indole serotonin receptor agonist is (R)-3-[(1-methyl-2-pyrrolidinyl)methyl]-1H-indole-5-[2-(phenylsulfonyl)ethyl], also referred to as Eletriptan.

In some embodiments, the indole serotonin receptor agonist is R-(+)3-methylamino-6-carboxamido-1,2,3,4-tetrahydrocarbazole, also referred to as Frovatriptan.

Adhesives

The adhesive layer comprises adhesives commonly in use for medical applications, such as polymeric adhesives, including but not limited to, e.g., acryl-type, synthetic rubber-type, and natural rubber-type materials.

Acryl-Type Adhesives

In some embodiments, the adhesive is a copolymer of alkyl (meth)acrylates, present in an amount of 40 wt % or more. In some embodiments, a copolymer of one type or two types or more of alkyl (meth)acrylates and one type or two types of more of copolymerized monomer is used. In some embodiments, a copolymer of one type or two types or more of alkyl (meth)acrylates is present in an amount of from about 50 wt % to about 98 wt %; and one type or two types of more of copolymerized monomer is present in an amount of from about 2 wt % to about 50 wt %.

Suitable alkyl (meth)acrylates include esters of from a primary to a tertiary alcohol, e.g., where the carbon number of the alkyl group is from 2 to 18, or from 4 to 12. In some embodiments, acrylic acid or methacrylic acid is used. Suitable copolymerized monomers generally have at least one unsaturated double bond that participates in the copolymerization reaction, or a monomer that has functional groups on the side chain. Functional groups include, e.g., a carboxyl group such as (meth) acrylic acid, itaconic acid, maleic acid, sulfoxyl group such as styrene sulfonic acid, sulfopropyl (meth)acrylate, allylsulfonic acid; a hydroxyl group such as (meth) hydroxyethyl acrylate, (meth) hydroxypropyl acrylate; an amino group such as aminoethyl (meth)acrylate, dimethylaminoethyl (meth)acrylate; an amide group such as (meth) acrylamide, dimethyl (meth) acrylamide, N-butyl acrylamide; and an alkoxyl group such as methoxyethyl (meth)acrylate, methoxyethylene glycol (meth)acrylate, methoxy polyethylene glycol (meth) acrylate.

Other monomers that are suitable for copolymerization include, but are not limited to, N-vinyl-2-pyrrolidone, methyl vinyl pyrrolidone, (meth) acrylonitrile, vinyl acetate, vinyl propionate, vinyl piridine, vinyl piperidone, vinyl pyrimidine, vinyl piperadine, vinyl pyrazine, vinyl pyrrol, vinyl imidazole, vinyl caprolactam, vinyl oxazole, and vinyl morpholine.

Suitable acryl-type adhesives include, but are not limited to, acrylic acid-octylacrylate copolymer; 2-ethylhexyl acrylate-vinyl pyrrolidone copolymer solution; 2-methoxyethyl acrylate-vinyl acetate copolymer; 2-ethylhexyl acrylate-2-ethylhexyl methacrylate-dodecyl methacrylate copolymer; and methyl acrylate-2-ethylhexyl acrylate copolymer resin emulsion.

Synthetic Rubber Adhesives

Suitable synthetic rubber-type adhesives include, but are not limited to, styrene-isoprene-styrene block copolymer, polyisobutylene, isoprene rubber, styrene-butadiene-styrene block copolymer, styrene-butadiene rubber, and silicon rubber. The adhesive will in some comprise one type of synthetic rubber. In other embodiments, the adhesive will include two or more types of synthetic rubber.

In some embodiments, a synthetic rubber-type adhesive or a natural rubber-type adhesives will have low adhesion. In these embodiments, one or more adhesion enhancers will be added to enhance adhesion. Suitable adhesion enhancers include, but are not limited to, polyterpene resin type, petroleum resin type, rosin type, rosin ester type, and oil-soluble phenol.

Hydrophobic Oil

In certain embodiments, the adhesive layer of a subject transdermal delivery systems includes an indole serotonin receptor agonist and one or more hydrophobic oils. The hydrophobic oil component of the adhesive layer of these embodiments softens the adhesive base and helps the adhesive adhere to the skin. Hydrophobic oils include higher fatty acid esters; oils and fats; higher fatty acids; and higher alcohols.

The hydrophobic oil is present in the adhesive layer in an amount of from about 2 weight % to about 50 weight %, e.g., from about 2 weight % to about 5 weight %, from about 5 weight % to about 10 weight %, from about 10 weight % to about 20 weight %, from about 20 weight % to about 30 weight %, from about 30 weight % to about 40 weight %, or from about 40 weight % to about 50 weight %. In some embodiments, hydrophobic oil is present in the adhesive layer in an amount of from about 5 weight % to about 40 weight %, from about 5 weight % to about 30 weight %, from about 5 weight % to about 20 weight %, from about 10 weight % to about 40 weight %, from about 10 weight % to about 30 weight %, from about 15 weight % to about 40 weight %, or from about 15 weight % to about 30 weight %. Suitable fatty acid esters include, but are not limited to, isopropyl myristate, isopropyl palmitate, octyldodecyl myristate, cetyl octanoate, hexyl laurate, myristyl lactate, diethyl sebacate, dioctyl sebacate, dioctyl succinate, dioctyl adipate, propylene glycol dicapriate, glyceryl trioctanoate, triglyceryl (octanate/decanate), medium-chain triglyceride, lauryl pyrrolidone carboxylate, and lauryl nicotinate.

Suitable oils and fats include, but are not limited to, squalene, liquid paraffin, lanolin, mineral oil, olive oil, and orange oil.

Suitable higher fatty acids include, but are not limited to, myristic acid, palmitic acid, lauric acid, capric acid, stearic acid, oleic acid, linoleic acid, and monocaprin acid.

Suitable higher alcohols include, but are not limited to, myristyl alcohol, oleyl alcohol, lauryl alcohol, cetyl alcohol, hexyldecanol, and isostearyl alcohol.

Additional Components

The adhesive layer of a subject transdermal delivery system will in some embodiments include, in addition to the above-discussed components, one or more additional components. Additional components include, but are not limited to, a transdermal absorption enhancer, a preservative (e.g., paraben), an antioxidant, a stabilizing agent, a filling agent that contains a hydrophilic polymer; a cross-linking agents; and a plasticizing agent, except for the aforementioned hydrophobic oil components.

Absorption Enhancers

Suitable transdermal absorption enhancers include any compound that promotes transdermal absorption. Suitable transdermal absorption enhancers include, but are not limited to, lauryl diethanolamide, tetraethyl glycol laurylate, glycerine monolaurate, sorbitan trioleate, and polyoxyethylen laurylate. If a transdermal absorption enhancer is present in the adhesive layer, the transdermal absorption enhancer is typically present in an amount of from about 0.01 weight % to about 20 weight %, from about 0.1 weight % to about 10 weight %, or from about 0.5 weight % to about 5 weight %. When the content of the transdermal absorption enhancer is more than 20 wt %, the skin irritation is observed. When it is less than 0.01 wt %, the effect of transdermal absorption is not observed.

Backing Layer

The adhesive composition, which includes an adhesive, an indole serotonin receptor agonist, and a hydrophobic oil, is typically present on a support or backing. The support is generally made of a flexible material which is capable of fitting in the movement of human body and includes, for example, various non-woven fabrics, woven fabrics, spandex, flannel, or a laminate of these materials with polyethylene film, polyethylene glycol terephthalate film, polyvinyl chloride film, ethylene-vinyl acetate copolymer film, polyurethane film, and the like.

Suitable backing layer materials include, but are not limited to, polyethylene terephthalate, polyethylene, polypropylene, vinyl acetate-vinyl chloride copolymer, polyurethane, acetylcellulose, ethylcellulose, soft polyvinyl chloride, polyvinylidene chloride, polytetrafluoroethylene, polyamide, paper, a single film of metal foil such as aluminum foil or a laminated film of foil, woven or unwoven fabric made from the aforementioned materials, and combined materials with the aforementioned films.

Release Film

In addition to the adhesive composition and the support layer, a subject transdermal delivery system may also include a release film 16 on the surface of the adhesive layer and opposite the backing, which release film provides for protection of the adhesive layer from the environment. The release film may be any convenient material, where representative release films include polyesters, such as PET (polyethylene terepthalate) or PP (polypropylene), and the like.

In certain embodiments, a subject transdermal delivery system (e.g., a patch) is present in a sealed package. Generally, the sealed package is fabricated from a packaging material that includes a layer made out of a material capable of preventing passage of moisture, oxygen and other agents, i.e., the package includes in a moisture/oxygen barrier material. Any suitable barrier material may be employed, where barrier materials of interest include metallic layers, e.g., aluminum, where in certain embodiments, the barrier layer is an aluminum layer. This barrier layer has a thickness sufficient to provide for the barrier function, where the thickness may range from about 5 to 15, such as from about 6 to 10 µm. In certain embodiments, the package is a laminate of the barrier layer in combination with one or more additional layers, e.g., polymeric layers, paper layers, etc. A representative aluminum containing package that may be used with the subject patch preparations is sold by Dainippon Printing Co., Ltd. (Kyoto, Japan).

A subject transdermal delivery system is manufactured using any known method. For example, in some embodiments, components such as an indole serotonin receptor agonist and a hydrophobic oil, as described above, are added to an organic solvent solution that includes the adhesive material(s); the solution is mixed, then pasted onto the release liner, and dried. When the adhesive base is pasted in a hot melt method, the adhesive polymer components are first dissolved; then other components (e.g., an indole serotonin receptor agonist and a hydrophobic oil) are added and pasted onto the release liner.

One convenient protocol for fabrication of a subject transdermal delivery system includes preparing an adhesive paste through the uniform mixing of the aforementioned ingredients and then coating the paste onto the support, followed by cutting of the resultant product to the specified size to obtain the desired transdermal patch preparation. The resultant transdermal patch preparation is then heat-sealed, typically several sheets to a package, using a packaging material containing an aluminum layer, as described supra, to obtain the sealed transdermal patch. For a more detailed description of the fabrication protocol, see U.S. Pat. No. 5,827,529; the disclosure of which is herein incorporated by reference.

In a fabrication protocol according to an embodiment of the invention, the adhesive composition is produced by using a mixer to uniformly blend the aforementioned ingredients by means of any convenient protocol into a paste, which is then spread by means of a spreader onto a backing or support material. As indicated above, the support material may be, for example, paper, or a woven or nonwoven cloth made of PET or PP or some other polyester fiber. For protection, the surface thereof is then covered with a release film of a polyester such as PET or PP. In some embodiments, a subject transdermal delivery system is self-adhesive, i.e., inherently adhesive, and thus may be fixed in a position over the skin, i.e., removably bonded to and/or about a given skin surface, without the use of additional adhesives or other means to hold the transdermal delivery system in place over the formulation.

As the adhesive compositions are adhesive, when applied to human skin they remain stably positioned at the site of application. As such, application of force is required to remove the adhesive compositions from the site of application. While application of force is required for removal, the adhesive compositions are not so adhesive such that removal of the compositions irritates or wounds the skin site to which the compositions were applied. In certain other embodiments a subject transdermal delivery system may be held in a fixed position on a skin surface using a separate adhesive such as an adhesive backing or the like or a combination of inherent adhesiveness and an additional separate adhesion means may be employed.

A subject transdermal delivery system is in certain embodiments, a patch. The shape of the patch may vary, where shapes of interest include, but are not limited to: square, rectangle, oval, circle, etc. The size of the patch may also vary, where in certain embodiments the size ranges from about 1 to 200 $cm^2$. This transdermal patch preparation may then packaged by means of a heat seal in a packaging material that includes a layer of aluminum to obtain the final product. It should be noted that the above manufacturing protocols are merely representative. Any convenient protocol that is capable of producing a subject transdermal delivery system, as described above, may be employed.

Kits

Also provided are kits, where the subject kits at least include one or more transdermal formulations as well as instructional material for using the same, e.g., in the methods of the invention. In certain embodiments, the kits include one or more transdermal delivery systems (e.g., patches), as described above. A subject transdermal delivery system in a subject kit may be present in a package, as described supra. The transdermal delivery systems of the kits may be present in individual pouches or analogous containers, to preserve the composition of the patches until use.

The subject kits also may include instructions for how to use the patches, where the instructions typically include information about where to apply the patch, dosing schedules etc. The instructions may be recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g. CD-ROM, diskette, etc.

The following examples are offered by way of illustration and not by way of limitation.

EXAMPLES

Example I

Practical Examples

A. Preparation of the Tape Formulation
1) Styrene/Isoprene/Styrene Block Copolymer Tape Preparation Based on the formulation shown in table 1, below, the tape formulations of the practice examples 1, 2, 4, 5, 6, 7 and the comparison example 1 were prepared in the following method. Styrene/isoprene/styrene block copolymer (Quintac 3570C, or Quintac 3421; Zeon Corporation), hydrogenated rosin glycerin ester (KE-311; Arakawa Chemical Industries, LTD.), liquid paraffin (Hi-Call M-352; Kaneda Co., LTD.), dibutylhydroxytoluene (BHT-F; Takeda-Kirin Foods Corporation) were dissolved in toluene to make adhesive base solution. In this solution, triptan, isopropyl myristate (NILLOL IPM-100; Nikko Chemicals Co., LTD.) and diethanolamine laurate (Profan AA-62EX; Sanyo Chemicals Co., LTD.) dissolved in ethyl acetate or isopropanol was added and stirred sufficiently, and the mixture was extended on the PET release liner in 100 μm thickness after drying, and dried to make the adhesive layer. Then, the adhesive layer was attached to the PET supporter (25 μm in thickness) to make tape formulation.

2) Acryl Adhesive Tape Formulation

Based on the formulation shown in Table 1, the tape formulations of the practice example 3 and the comparison example 2 were prepared. The specified weight (converted to solid weight) of acryl ester adhesive (MASCOS631; Cosmed) was weighed, and triptan, isopropyl myristate (NILLOL IPM-100; Nikko Chemicals Co., LTD.) and diethanolamine laurate (Profan AA-62EX; Sanyo Chemicals Co., LTD.) dissolved in ethyl acetate or isopropanol were added to the solution, and stirred sufficiently. The mixture was extended on the PET release liner in 100 μm thickness after drying, and dried to make the adhesive layer. Then, the adhesive layer was attached to the PET supporter (25 μm in thickness) to make tape formulation.

TABLE 1

Test formulations

| | Com. Ex. 1 | Ex. 1 | Ex. 2 | Com. Ex. 2 | Ex. 3 | Ex. 4 | Ex. 5 | Ex. 6 | Ex. 7 |
|---|---|---|---|---|---|---|---|---|---|
| Styrene-isoprene-styrene block copolymer(3421) | 41 | — | — | — | — | — | — | — | — |
| Styrene-isoprene-styrene block copolymer(3570C) | — | 15 | 15 | — | — | 20 | 20 | 20 | 20 |
| Hydrogenated rosin glycerol ester | 50 | 40 | 40 | — | — | 50 | 50 | 50 | 50 |
| Liquid paraffin | — | 36 | 21 | — | — | 1 | 1 | 1 | 1 |
| Dibutylhydroxytoluene | 1 | 1 | 1 | — | — | 1 | 1 | 1 | 1 |
| Acryl polymer | — | — | — | 96 | 74 | — | — | — | — |
| Isopropyl miristate | — | — | 15 | — | 17 | 15 | 15 | 15 | 15 |
| Lauryl diethanolamide | — | — | — | — | 5 | 5 | 5 | 5 | 5 |
| Zolitriptan | 8 | 8 | 8 | 4 | 4 | 8 | — | — | — |
| Sumatriptan succinate | — | — | — | — | — | — | 8 | — | — |
| Eletriptan | — | — | — | — | — | — | — | 8 | — |
| Rizatriptan benzoate | — | — | — | — | — | — | — | — | 8 |

B. In Vitro Skin Permeability Test

The tape formulations obtained in the practice examples and comparison examples described above were punched into 14 mm diameter circular patch, and applied in the middle of the extracted skin of hairless mice (7 weeks old, female; Japan SLC, Inc.) and immobilized in the Franz vertical cell (capacity 10 mL, 15 mm diameter). Then, the receptor fluid (phosphate buffer pH 7.4) was sampled time-dependently to analyze the drug permeability with high performance liquid chromatography.

Figure 2:
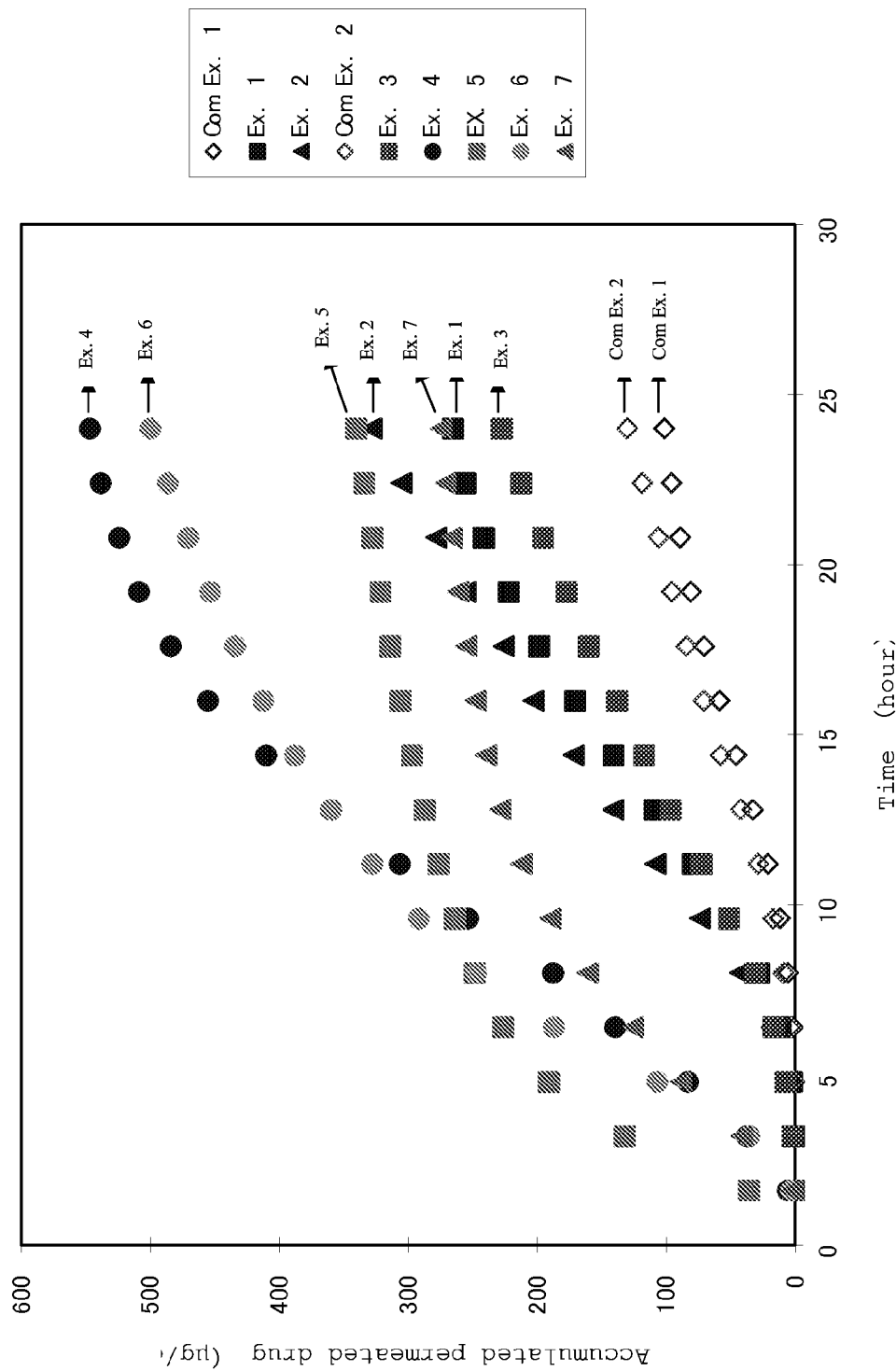
FIGS. 2 & 3 provide graphical representations of results reported in the Experimental section, below.

The result is shown in FIG. 2. This result indicates that inclusion of hydrophobic oil in the adhesive formulation increases the skin permeability of triptans significantly, and addition of penetration enhancer remarkably increases the skin permeability of triptans.

C. Blood Analysis in Rats

Figure 3:
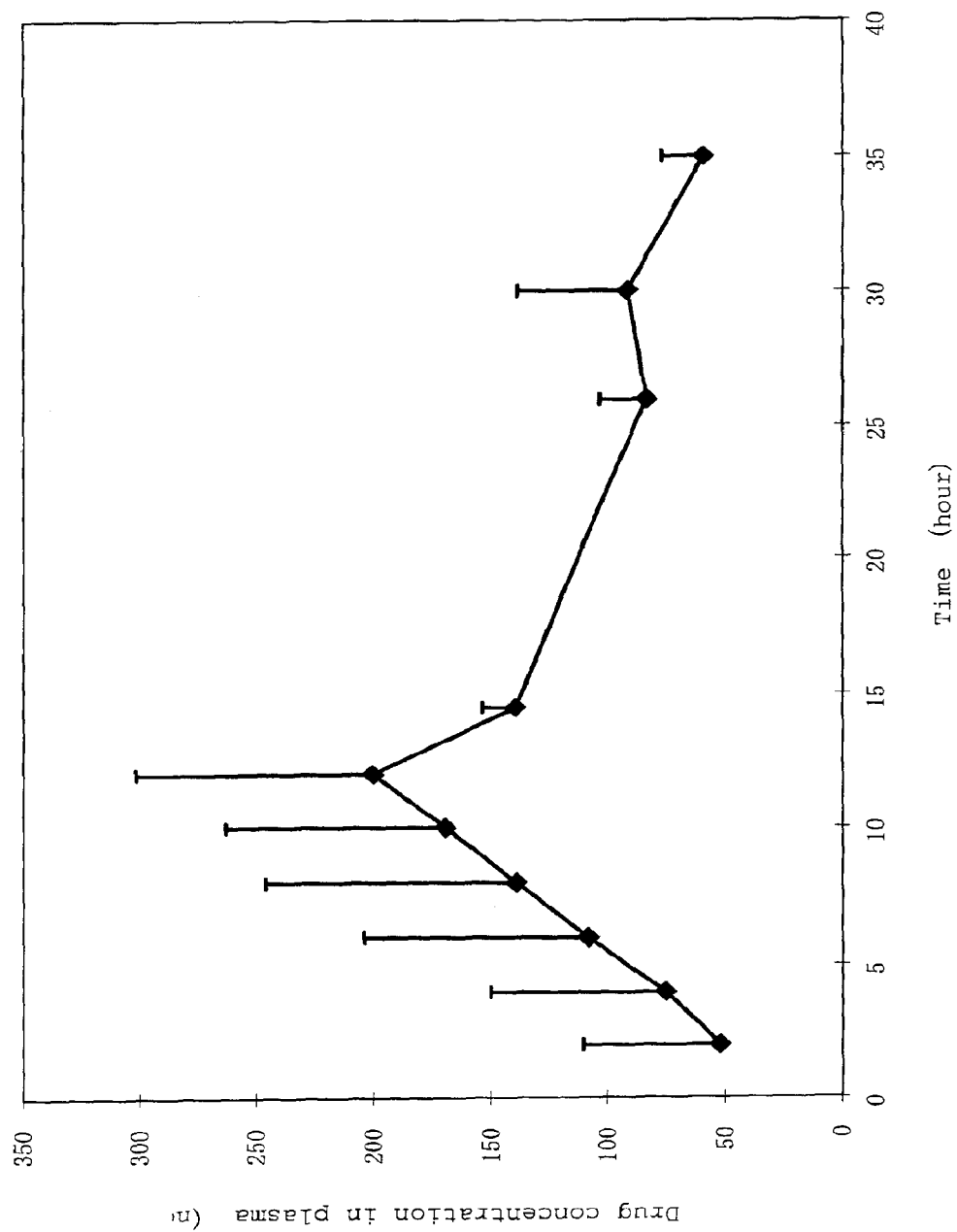

The tape formulation obtained in the practice example 1 was punched into 4×5 cm, and applied on the back of the depilated Wister rats (Japan SLC, 12 weeks old, male). The blood was sampled time-dependently, and centrifuged to obtain the plasma and the drug concentration was analyzed with LC/MS/MS. The result is shown in FIG. 3. This result indicates that the transdermal formulation of triptans maintains the blood concentration of triptans for a long period.

D. Test in Human

1. The tape formulation obtained in the practice example 1 was punched into 6×6 cm to prepare the samples. The sample was applied for 24 hours on the upper arm of the female volunteer (49) with migraine when she felt the sign of migraine. As a result, the volunteer did not experience the migraine attack during the application period of the tape, and it was found that the transdermal triptan prevents migraine attack. During and after the application of the tape formulation, no skin irritation or pruritus was observed in the application site.

2) The tape formulation obtained in the practice example 1 was punched into 6×6 cm to prepare the samples. The sample was applied for 24 hours on the upper arm of the female volunteer (52) with migraine during the migraine attack. As a result, following the application of the tape formulation, the migraine symptom disappeared and it did not resume. It was found that the transdermal triptan has durable analgesic effect for migraine. During and after the application of the tape formulation, no skin irritation or pruritus was observed in the application site.

Example II

Preparation of Another Transdermal Delivery System

An adhesive polymer(s) is blended with the other ingredients listed in Table 2 into uniformity and adjusted into a paste, which is then spread onto a backing layer; the resulting product is then laminated with a PET film and then cut into rectangles or squares.

TABLE 2

| Component | Weight % |
|---|---|
| Adhesive polymer | 76.2 |
| Isopropyl myristate | 15.2 |
| Diethanolamine laurate | 4.8 |
| Zolmitriptan | 3.8 |

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A transdermal formulation comprising:
a) an adhesive layer comprising:
an indole serotonin receptor agonist,
an adhesive polymer base comprising a rubber type adhesive or an acryl type adhesive,
a hydrophobic oil selected from the group consisting of isopropyl myristate, liquid paraffin and combinations thereof, and
an absorption enhancing agent selected from the group consisting of lauric acid diethanolamide, tetraethylene glycol laurate, glycerol monolaurate, sorbitan trioleate, and a polyol; and
b) a backing layer.

2. The transdermal formulation of claim 1, wherein said agonist is present in an amount of from about 0.5 weight % to about 50 weight %.

3. The transdermal formulation according to claim 1, wherein said hydrophobic oil is present in an amount of from about 2 weight % to about 50 weight %.

4. The transdermal formulation of claim 1, wherein said indole serotonin receptor agonist is selected from sumatriptan, frovatriptan, zolmitriptan, eletriptan, rizatriptan, naratriptan, and almotriptan.

5. The transdermal formulation of claim 1, wherein the absorption enhancing agent is present in an amount of from about 0.01 weight % to about 20 weight %.

6. The transdermal formulation of claim 1, further comprising a detachable protective layer.

7. The transdermal formulation of claim 1, wherein said transdermal formulation is a patch.

8. The transdermal formulation of claim 1, wherein the indole serotonin receptor agonist comprises a triptan type drug.

9. The transdermal formulation of claim 1, wherein the indole serotonin receptor agonist is selected from the group consisting of sumatriptan, eletriptan, rizatriptan and zolmitriptan.

10. The transdermal formulation of claim 1, wherein the rubber type adhesive comprises a polymer selected from the group consisting of styrene-isoprene-styrene block copolymer, polyisobutylene, isoprene rubber, styrene-butadiene-styrene block copolymer, styrene-butadiene rubber, silicon rubber and combinations thereof.

11. The transdermal formulation of claim 1, wherein the adhesive layer further comprises an adhesion enhancer.

12. The transdermal formulation of claim 11, wherein the adhesion enhancer is selected from the group consisting of a polyterpene resin, a petroleum resin, a rosin, a rosin ester, and an oil-soluble phenol.

13. The transdermal formulation of claim 12, wherein the rosin ester comprises a hydrogenated rosin glycerol ester.

14. The transdermal formulation of claim 1, wherein the adhesive layer further comprises an antioxidant.

15. The transdermal formulation of claim 14, wherein the antioxidant comprises dibutylhydroxytoluene.

16. A transdermal formulation comprising:
a) an adhesive layer comprising:
an indole serotonin receptor agonist comprising a triptan type drug,
an adhesive polymer base comprising a rubber type adhesive or an acryl type adhesive,
a hydrophobic oil selected from the group consisting of isopropyl myristate, liquid paraffin and combinations thereof,
an adhesion enhancer selected from the group consisting of a polyterpene resin, a petroleum resin, a rosin, a rosin ester, and an oil-soluble phenol, and
an antioxidant; and
b) a backing layer.

17. A method of delivering a therapeutic amount of an indole serotonin receptor agonist to an individual in need thereof, the method comprising contacting a topical surface of said individual with a transdermal formulation comprising said indole receptor serotonin agonist, wherein the transdermal formulation is a formulation according to claim 1.

18. The method according to claim 17, wherein said transdermal formulation is a patch.

19. The method according to claim 18, wherein said method comprises adhering said patch formulation to a skin surface of the individual.

20. The method of claim 17, wherein said method treats headache.

21. The method of claim 17, wherein the method provides for a level of indole serotonin receptor agonist in the individual that is effective to treat migraine pain.

22. A method of treating an individual for a headache, said method comprising: contacting a topical surface of said individual with a transdermal formulation according to claim 1.

* * * * *